United States Patent
Tong et al.

(10) Patent No.: US 11,041,180 B2
(45) Date of Patent: Jun. 22, 2021

(54) COMPLEX BACTERIA FOR IMPROVING CORN STEEPING EFFECTS AND USAGE THEREOF

(71) Applicant: COFCO (Jilin) Bio-Chemical Technology Co., Ltd., Jilin (CN)

(72) Inventors: Yi Tong, Beijing (CN); Yi Li, Beijing (CN); Jin Tao, Beijing (CN); Bo Chen, Beijing (CN); Yuan Zhang, Beijing (CN)

(73) Assignee: COFCO (Jilin) Bio-Chemical Technology Co., Ltd., Jilin (CN)

( * ) Notice: Subject to any disclaimer, the term of this patent is extended or adjusted under 35 U.S.C. 154(b) by 0 days.

(21) Appl. No.: 16/823,669

(22) Filed: Mar. 19, 2020

(65) Prior Publication Data

US 2020/0299739 A1    Sep. 24, 2020

(30) Foreign Application Priority Data

Mar. 20, 2019  (CN) .......................... 201910220358.8

(51) Int. Cl.
| | | |
|---|---|---|
| *C12P 19/04* | (2006.01) |
| *C12N 1/20* | (2006.01) |
| *C12R 1/07* | (2006.01) |
| *C12R 1/125* | (2006.01) |
| *C12R 1/10* | (2006.01) |

(52) U.S. Cl.
CPC ................ *C12P 19/04* (2013.01); *C12N 1/20* (2013.01); *C12R 1/07* (2013.01); *C12R 1/10* (2013.01); *C12R 1/125* (2013.01)

(58) Field of Classification Search
None
See application file for complete search history.

(56) References Cited

U.S. PATENT DOCUMENTS

| | | | |
|---|---|---|---|
| 2007/0065540 A1* | 3/2007 | Jones ........................ | C12N 1/16 426/53 |
| 2016/0002690 A1* | 1/2016 | Long ..................... | C08B 30/044 435/99 |
| 2020/0140909 A1* | 5/2020 | Gibbons ................ | C12N 9/248 |

FOREIGN PATENT DOCUMENTS

| | | | | |
|---|---|---|---|---|
| CN | 102839140 A | 12/2012 | | |
| CN | 108251320 A | 7/2018 | | |
| CN | 108251324 A | 7/2018 | | |
| CN | 109517761 A | 3/2019 | | |
| WO | WO-2010027846 A1 * | 3/2010 | ........... | C08B 30/044 |

* cited by examiner

*Primary Examiner* — Nghi V Nguyen
(74) *Attorney, Agent, or Firm* — Duane Morris LLP

(57) ABSTRACT

Provided a complex bacteria for improving the corn steeping effects and usage thereof. The complex bacteria comprises strains capable of producing protease, cellulase and hemicellulase. Using the complex bacteria to steep corn, effects of reducing the addition amount of $SO_2$, shortening the steeping time and improving the starch yield are achieved.

8 Claims, No Drawings

COMPLEX BACTERIA FOR IMPROVING CORN STEEPING EFFECTS AND USAGE THEREOF

FIELD

The present disclosure relates to the technical field of corn deep-processing, particularly relates to a complex bacteria for improving the corn steeping effects, an use of the complex bacteria in corn steeping, and a method for improving the corn steeping effects.

BACKGROUND

The production of corn starch may be categorized into a dry process and a wet process. The dry process is to separate out germ and fiber by means of grinding, sieving and selection by winnowing to obtain low-fat corn flour. The wet process is to separate germ, fiber and protein from corn by means of steeping, coarse and fine grinding so as to produce the corn starch with high-purity. At present, an enclosed wet process is generally adopted in order to produce the corn starch with high-purity.

Corn steeping is the first step in a wet process for producing corn starch, it is also the first and most important process for extracting starch. This step directly influences the yield and quality of various products in the starch industry. The main purpose of steeping is to soften the corn kernels, allowing the steeped corn having a water content of about 45%. The leached soluble substances mainly comprise minerals, proteins, carbohydrate and its analogues; the steeping process mainly serves to destroy a protein network structure to separate starch from protein; and in the steeping process, it is also required to prevent pollution from miscellaneous bacteria, inhibit the oxidation reaction, and avoid the discoloration of starch. The conventional process needs to add 2,000-5,000 ppm of high-concentration $SO_2$ into the steeping solution, and steep corn in the solution at a high temperature of 48-55° C. for 48-72 hours, so as to fully disrupt the protein net coated on the outer side of the starch, and achieve the desirable effects of corn steeping and separation. The dispersion effect of the sulfur dioxide-containing steeping water on the protein network is enhanced along with an increased content of sulfur dioxide. When the concentration of sulfur dioxide is within a range of 2,000-3,000 ppm, it has an appropriate dispersion effect on the protein net, and the starch is easy to be separated; when the concentration of sulfur dioxide is less than 1,000 ppm, it does not produce sufficient dispersion effect, and the starch separation is difficult. However, a use of large quantity of $SO_2$ may cause many problems, such as environmental pollution, corrosion of equipment, and excessive sulfurous acid residue in the starch products.

In addition, the steeping step needs the longest time in the whole production process, and consumes a large amount of energy, as a result, the excessively long steeping time period is also the bottleneck problem affecting production efficiency of the corn starch.

At present, there are some emerging corn processing methods, such as a single or a complex enzyme preparation is utilized for facilitating corn steeping and starch production, but the enzyme preparation requires relatively high cost, and the production conditions cannot be easily controlled, thus the methods have not been widely used. Moreover, the process of corn steeping assisted by microbial fermentation produces favorable effects on the steeping process by means of adding a kind of microbe or microbial fermentation product into the steeping solution. The Thermophilic *lactobacillus, Aspergillus fumigatus, Bacillus* and so on are reported to be added for assisting the steeping process at present, but each of which merely involves a single microbial action, and the steeping process is required to make many modifications in some circumstances.

Therefore, the development of a novel process which can shorten the steeping time, reduce the dosage of $SO_2$ and does not require significantly modification on the existing steeping process will plays an important role in improving the wet process for processing corn starch.

SUMMARY

For the sake of overcoming the above problems in the prior art, the present disclosure provides a complex bacteria, the usage of the complex bacteria can greatly shorten the steeping time of corn and reduce the dosage of $SO_2$, and the steeping flow of corn is not required to be modified.

In order to fulfill the above purposes, a first aspect of the present disclosure provides a complex bacteria for improving the corn steeping effects, the complex bacteria comprises strains capable of producing protease, cellulase and hemicellulase.

In a second aspect, the present disclosure provides an use of the aforementioned complex bacteria in corn steeping.

In a third aspect, the present disclosure provides a method for improving corn steeping effects, the method comprises: steeping corn in a steeping solution containing the aforementioned complex bacteria.

According to the present disclosure, several microbes with different functions are utilized to ferment and generate functional enzymes such as protease, hemicellulase and cellulase, which are combined into a corn steeping section, thereby producing the effects of reducing the addition amount of $SO_2$, shortening the steeping time and improving the starch yield based on the microbial community clustering effect.

DETAILED DESCRIPTION

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to produce one or more new numerical ranges, which should be deemed have been specifically disclosed herein.

In a first aspect, the present disclosure provides a complex bacteria for improving the corn steeping effects, wherein the complex bacteria comprises strains capable of producing protease, cellulase and hemicellulase.

It shall be indicated in the present disclosure that the "complex bacteria" does not strictly refer to the combination of multiple strains, specifically, it can be determined according to actual conditions, for example, when a strain can simultaneously produce protease, cellulase and hemicellulase, the complex bacteria may be a single strain; when a single strain cannot simultaneously produce protease, cellulase and hemicellulase, the combination of multiple strains is required.

According to the present disclosure, it is preferable that the complex bacteria further comprises strains capable of producing lactic acid, in order to further shorten the steeping time, reduce the concentration of $SO_2$, and improve the starch yield.

According to the present disclosure, in order to desirably enable the steeping solution to penetrate into corn particles, destroy the network structure of protein, and release starch particles combined on protein or cellulose during the corn steeping process, an addition of the complex bacteria for producing lactic acid, protease, cellulase and hemicellulase can generate positive effects on corn steeping; however, for the sake of avoiding loss of dissolved starch resulting from the generation of excessive amylase, the complex bacteria preferably does not produce amylase. Wherein, the term "does not produce amylase" means that the diameter of a transparent zone around a bacterial colony is within 1.5 times of the diameter of the bacterial colony, or there is not an obvious transparent zone, after the bacterial is inversely cultured on a starch screening plate at 48° C. for 24 hours.

Wherein the starch screening plate may be a starch screening plate which is conventionally used in the technical field and is applicable to the corresponding strains, it may be commercially available, or be prepared by oneself.

According to the present disclosure, the strains in the complex bacteria can be selected in a wide range as long as the strains can simultaneously produce protease, cellulase and hemicellulase, and further preferably can simultaneously produce lactic acid, protease, cellulase and hemicellulase. However, the inventors of the present disclosure have found in researches that when the bacterial species in the complex bacteria is selected from *Bacillus*, it can further reduce the addition amount of $SO_2$, shorten the steeping time and improve the starch yield.

Preferably, the *Bacillus* is selected from the group consisting of *Bacillus coagulans, Bacillus subtilis*, and *Bacillus licheniformis*.

According to the present disclosure, in order to exert the maximum synergistic effect of the microbial community among the microorganisms during the steeping process, the strains in the complex bacteria are preferably microbes resistant to high temperature, for example, resistant to high temperature of 45-60° C. Therefore, the *Bacillus coagulans* is preferably CGMCC No. 6382; the *Bacillus subtilis* is preferably CGMCC No. 13139; the *Bacillus licheniformis* preferably selects from CGMCC No. 13313 and CGMCC No. 15012.

According to a particularly preferred embodiment of the present disclosure, the complex bacteria comprises *Bacillus coagulans* CGMCC No. 6382, *Bacillus subtilis* CGMCC No. 13139, *Bacillus licheniformis* CGMCC No. 13313 and *Bacillus licheniformis* CGMCC No. 15012.

According to the present disclosure, the complex bacteria can be added into the corn steeping solution in the form of a solid preparation or a fermentation broth; according to a preferred embodiment of the present disclosure, the complex bacteria is added into the corn steeping solution in the form of the fermentation broth.

The fermentation broth of the complex bacteria can be prepared according to the conventional method in the technical field, for example, the fermentation can be implemented in a culture medium containing peptone, yeast extract powder, sodium chloride, glucose and corn pulp filtrate, so as to obtain the fermentation broth. According to a preferred aspect of the present disclosure, the culture medium comprises 0.8-1.2% of peptone, 0.4-0.6% of yeast extract powder, 0.4-0.6% of sodium chloride, 0.8-1.2% of glucose, 4-6% (v/v) of corn pulp filtrate based on the unit of g/100 ml, and it has a pH within a range of 5.5-6.5.

Wherein the corn pulp filtrate is a solution obtained by filtering concentrated corn pulp with the dry solid content of 35-45% (g/100 ml) to remove insoluble solids, the corn pulp is a steeping solution obtained after completing the process of steeping corn, the corn pulp is then subjected to concentrating process to obtain the concentrated corn pulp with the dry solid content of 35-45% (g/100 ml).

Wherein the fermentation conditions may be the conventional fermentation conditions in the art, according to a preferred embodiment of the present disclosure, the strain is cultured in the culture medium at the temperature of 45-55° C. and the rotation speed of 120-180 rpm for 20-30 hours, and then inoculated in the culture medium at the temperature of 45-55° C. and the rotation speed of 120-180 rpm for activation for 16-20 hours.

According to the present disclosure, the ratio of each strain in the complex bacteria can be selected in a wide range, as long as the complex bacteria can generate protease, cellulase and hemicellulase, preferably lactic acid, protease, cellulase and hemicellulose after being added into the steeping solution. Preferably, when the complex bacteria comprises *Bacillus coagulans* CGMCC No. 6382, *Bacillus subtilis* CGMCC No. 13139, *Bacillus licheniformis* CGMCC No. 13313 and *Bacillus licheniformis* CGMCC No. 15012, the bacterial cell ratio of *Bacillus coagulans* CGMCC No. 6382, *Bacillus subtilis* CGMCC No. 13139, *Bacillus licheniformis* CGMCC No. 13313 and *Bacillus licheniformis* CGMCC No. 15012 is 1:(0.1-10):(0.1-10): (0.1-10), more preferably 1:(0.4-5):(0.4-5):(0.4-5). In the present disclosure, the number of bacterial cells is calculated in colony-forming unit (CFU), and the number of bacterial cells may be measured in accordance with the national standard GB 4789.2-94 in China.

According to the present disclosure, the complex bacteria can be obtained by inoculating all the desired strains into a culture medium for cultivation, or can be obtained by inoculating the desired strains into a culture medium separately for cultivation and subsequently mixing the cultured fermentation broth.

In a second aspect, the present disclosure provides a use of the aforementioned complex bacteria in corn steeping.

Using the complex bacteria provided by the present disclosure in the process of steeping corn can produce the effects of reducing the addition amount of $SO_2$, shortening the steeping time and improving the starch yield. As shown in the examples, the content of $SO_2$ in the steeping solution can be reduced from 2000-5000 ppm to 400-1200 ppm, and the steeping time can be shortened from 48 hours to 16-30 hours.

In a third aspect, the present disclosure provides a method for improving corn steeping effects, the method comprising: steeping corn in a steeping solution containing the aforementioned complex bacteria.

According to the present disclosure, the steeping solution further comprises $SO_2$, as previously mentioned, the addition of the complex bacteria provided by the present disclosure in the steeping process can significantly reduce the dosage of $SO_2$, and preferably, the concentration of $SO_2$ in the steeping solution is 400-1200 ppm.

Unless otherwise specified, the concentration of $SO_2$ in the present disclosure refers to the concentration of sulfurous acid calculated by $SO_2$.

According to the present disclosure, as mentioned above, the addition of the complex bacteria provided by the present disclosure in the steeping process can be significantly shorten the steeping time. In the present disclosure, the steeping time is measured based on the criteria that the steeped corn can be cracked by hand and the germ can be extruded. Preferably, the steeping time is within a range of 16-30 hours.

According to the present disclosure, the addition amount of the complex bacteria can be selected in a wide range, and preferably, the addition amount of the complex bacteria is 1-3 vol % based on the fermentation broth comprising the complex bacteria after the fermentation process.

The steeping temperature according to the present disclosure may be a commonly used steeping temperature in the art, for example, 48-55° C.

According to the present disclosure, the steeping solution may be a steeping solution conventionally used in the art, for example, hot water with a temperature of 48-55° C., both the complex bacteria of the present disclosure and sulfurous acid are added therein.

The addition amount of the steeping solution may be a conventional choice in the technical field, and preferably, the addition amount of the steeping solution is 200-500 ml based on 100 g of dry corn.

EXAMPLES

The present disclosure will be described in detail below with reference to examples. The examples are only intended for illustrating instead of limiting the present disclosure.

Unless otherwise specified, the reagents and culture media used in the following examples are commercially available, and the process used pertains to the conventional method.

(1) Strains

The *Bacillus coagulans* CGMCC No.6382 was derived from the Chinese patent CN102839140B titled "L-lactic acid producing strain separated and screened out of corn steeping water", and was deposited to China General Microbiological Culture Collection Center (CGMCC) (address: Institute of Microbiology under Chinese Academy of Sciences, Building 3, No. 1 Beichen West Road, Chaoyang District, Beijing postal code 100101) on Jul. 19, 2012 and numbered as CGMCC No. 6382.

The *Bacillus subtilis* CGMCC No.13139 was derived from the Chinese patent application CN108251324A having an application number "201611248898.X" and a title of invention "*Bacillus subtilis*, inoculant containing the same and application thereof, vomitoxin degradation method and kit", and was deposited to China General Microbiological Culture Collection Center (CGMCC) (address: Institute of Microbiology under Chinese Academy of Sciences, Building 3, No. 1 Beichen West Road, Chaouyang District, Beijing postal code 100101) on Oct. 24, 2016 and numbered as CGMCC No. 13139.

The *Bacillus licheniformis* CGMCC No.13313 was derived from the Chinese patent application CN108251320A having an application number "201611246221.2" and a title of invention "*Bacillus licheniformis*, microbial agent containing Bacillus licheniformis, application of *Bacillus licheniformis* and/or microbial agent, method for degrading zearalenone, and kit", and was deposited to China General Microbiological Culture Collection Center (CGMCC) (address: Institute of Microbiology under Chinese Academy of Sciences, Building 3, No. Beichen West Road, Chaoyang District, Beijing, postal code: 100101) on Nov. 16, 2016 and numbered as CGMCC No. 13313.

The *Bacillus licheniformis* CGMCC No.15012 was derived from the Chinese patent application CN109517761A having an application number "201811560739.2" and a title of invention "Cellulase-producing *Bacillus licheniformis*, microbial fermentation preparation thereof and application of cellulase-producing *Bacillus licheniformis*", and was deposited to China General Microbiological Culture Collection Center (CGMSS) (address: Institute of Microbiology under Chinese Academy of Sciences, Building 3, No. 1 Beichen West Road, Chaoyang District, Beijing, postal code 100101) on Dec. 4, 2017 and numbered as CGMCC No. 15012.

(2) Method

Simulation of countercurrent method for steeping process: 8 steeping tanks formed a group, the steeping temperature was maintained at 50° C., the steeping solution having a certain concentration of $SO_2$ (the concentration of sulfurous acid is converted into the concentration of $SO_2$ during the preparation process) was added into the last part of corn in the steep group (with the ratio of liquid to dry corn is 3:1 (v/m)), the steeping solution was transferred to the previous part of corn every 6 hours, and the steps were repeated, such that the new steeping solution with the highest concentration of $SO_2$ was contacted with the corn which had been steeped for the longest time, and the newly steeped corn was contacted with the last steeping solution with the lowest concentration of $SO_2$. The steeping solution after completion of the steeping process forms a thin corn pulp, the steeping solutions and the corns with different steeping time were taken for detecting the steeping effects.

Measurement of water content of steeped corn: the water on the surface of the steeped corn was drained off, about 20 g of the sample was weighted, the wet weight of the sample was accurately recorded and the sample was then placed in a weighing bottle which was dried to a constant weight, then the sample with the weighing bottle was put on an oven at a temperature of $105\pm2°$ C., the sample was dried to the constant weight, the dried sample was then placed in a dryer, and cooled to the ambient temperature, weighed and calculated the water content of steeped corn.

Measurement of corn starch yield: 100 g of steeped corn was taken, the actual wet weight of steeped corn was recorded, the corn was crushed through coarse grinding by a grinder, a small amount of water was added and stirred to enable germs to be suspended and separated, the part from which the germs were removed was then subjected to fine grinding to obtain a pulp, the pulp was filtered through a 200-mesh sieve, the filtered pulp was mixed with washing-up liquid obtained after washing the filter residue, and then stands still at 4° C., subjected to centrifugation at a rotational speed of 4,000 rpm for 3 min to remove protein, the lower-layer starch was collected, and dried to constant weight, the dried starch was weighed such that the corn starch yield was calculated.

(3) Culture Media

The percentages in the formulation have an unit of m/v, i.e., g/100 ml, unless otherwise specified.

Seed culture medium: comprises 2% of glucose, 1% of yeast powder and 20% (v/v) of thin corn pulp, it has a pH within a range of 5-6.

Activated culture medium: comprises 1% of peptone, 0.5% of yeast extract powder, 0.5% of sodium chloride, 1% of glucose and 5% (v/v) of corn pulp filtrate, it has a pH of 6. (The corn pulp filtrate is a solution obtained after removing insoluble solids from the concentrated corn pulp having a dry solid content of 40%).

Calcium carbonate screening plate: comprises 1% of peptone, 0.5% of yeast extract powder, 0.5% of sodium chloride, 2% of glucose, 2% (v/v) of corn pulp filtrate, 1% of calcium carbonate and 2% of agar, it has a pH of 5.

Skim milk screening plate: comprises 2% of skimmed milk powder and 2% of agar, it has a pH of 5.

Hemicellulose screening plate: comprises 2% of hemicellulose, 1% of peptone, 0.5% of yeast extract powder, 0.5% of sodium chloride and 2% of agar, it has a pH of 5.

CMC screening plate: comprises 2% of sodium carboxymethylcellulose (CMC), 1% of peptone, 0.5% of yeast extract powder, 0.5% of sodium chloride and 2% of agar, it has a pH of 5.

Starch screening plate: comprises 2% of corn starch, 1% of peptone, 0.5% of yeast extract powder, 0.5% of sodium chloride and 2% of agar, it has a pH of 5.

Acid production culture medium: comprises 1% of peptone, 0.5% of yeast extract powder, 0.5% of sodium chloride, 2% of glucose and 2% (v/v) of corn pulp filtrate, it has a pH of 6.

Detection of lactic acid in fermentation broth with a high performance liquid chromatography (HPLC): a chromatographic instrument: Agilent Technologies 1260 Infinity II; a detector: RID (Differential Refraction Index Detector); separation column: Aminex HPX-87H Column 300×7.8 mm; column temperature: 55° C.; mobile phase: 0.005M sulfuric acid; flow rate: 0.5 mL/min; sample injection amount: 20μL. The retention time of lactic acid is about 14 min.

Test Example

The test example was used for testing the performance of the strains used in the present disclosure The strains were respectively inoculated into an activated culture medium for activation cultivation at a temperature of 37° C. and a rotational speed of 150 rpm for 16 hours, then inoculated into a new activated culture medium according to the proportion of 1% by volume for cultivation at a temperature of 50° C. and a rotational speed of 150 rpm for 16 hours, the bacterial liquid with the growable strains was sequentially inoculated onto a calcium carbonate screening plate, a skim milk screening plate, a hemicellulose screening plate, a CMC screening plate and a starch screening plate, and then statically cultured at a temperature of 48° C. for 24 hours. The diameter size of the bacterial colony formed on each plate was observed and recorded.

The diameter of the transparent zone on a calcium carbonate screening plate, a skim milk screening plate and a starch screening plate was directly observed and recorded.

5 mL of 1% Congo red solution was added into the hemicellulose screening plate and the CMC screening plate respectively, subjected to standing still at the ambient temperature for 30 min, the Congo red solution was then removed, 1 mol/L sodium chloride solution was further added, subjected to standing still at the ambient temperature for 30 min, the sodium chloride solution was then removed, the diameter of a transparent zone around a bacterial colony was subsequently observed.

Wherein, the strain having a ratio of the diameter of transparent zone/colony diameter to be 3 or more was marked as "+++", the strain having a ratio of the diameter of transparent zone/colony diameter to be within a range of 1.5-3 was marked as "++", the strain having a ratio of the diameter of transparent zone/colony diameter to be less than 1.5 was marked as "+", the strain which did no exhibit an obvious transparent zone was marked as "−", the larger is the diameter of the transparent zone, the stronger is the enzyme activity.

The strain with larger transparent zone on the calcium carbonate screening plate was activated overnight by using an acid production culture medium at a temperature of 50° C. and a rotational speed of 150 rpm, the strain was then inoculated into the acid production culture medium according to the proportion of 5% by volume to cultivate at a temperature of 50° C. and a rotational speed of 150 rpm for 24 hours, a liquid chromatography was used for detecting whether the acid produced by the strains was lactic acid. The amount of the mark "+" represented the amount of produced lactic acid, and the mark "−" indicated that there was no lactic acid produced.

The test results for the strains were shown in Table 1.

TABLE 1

| Preservation No. | Classification | Acid production | Protein | Cellulose | Hemicellulose | Starch |
|---|---|---|---|---|---|---|
| CGMCC No. 6382 | Bacillus coagulans | +++ | − | + | + | − |
| CGMCC No. 13139 | Bacillus subtilis | + | +++ | + | − | − |
| CGMCC No. 13313 | Bacillus licheniformis | + | + | + | +++ | + |
| CGMCC No. 15012 | Bacillus licheniformis | − | ++ | +++ | ++ | − |

As can be seen from Table 1, The *Bacillus coagulans* CGMCC No. 6382, *Bacillus subtilis* CGMCC No. 13139, *Bacillus licheniformis* CGMCC No. 13313 and *Bacillus licheniformis* CGMCC No. 15012 can endure a high temperature of 50° C. and produce at least one of lactic acid, protease, cellulase and hemicellulase, but substantially do not produce amylase.

Example 1

This example used for illustrating the combined effects of 4 *Bacillus* strains.

Obtaining fermentation broth: 4 strains were respectively activated by an activated culture medium at a temperature of 50° C. and a rotational speed of 150 rpm for 24 hours, and then were inoculated into a seed culture medium according to the proportion of 3% (v/v) respectively, and subjected to a shake culture at a temperature of 50° C. for 16-20 hours, so as to obtain the mixed strain fermentation broth which was to be mixed with the steeping solution.

The corn was steeped according to the addition amount of $SO_2$ and mixed strain fermentation broth illustrated in Table 2, when to finish the steep was determined based on the criteria that the steeped corn can be cracked by hand and the germ can be extruded, the seed coat can be peeled off and was transparent and glossy, at this time the water content of the wet corn was in accordance with the standard of 40-46%.

The steeping time, the water content of the steeped corn, and the starch yield were shown in Table 2.

TABLE 2

| $SO_2$ concentration | Mixed strain fermentation broth | Steeping time | Water content of the steeped corn | Starch yield |
|---|---|---|---|---|
| 3000 ppm | 0 | 48 h | 43% | 65.1% |
| 1200 ppm | 2% | 30 h | 45% | 66.1% |

TABLE 2-continued

| SO$_2$ concentration | Mixed strain fermentation broth | Steeping time | Water content of the steeped corn | Starch yield |
|---|---|---|---|---|
| 800 ppm | 3% | 24 h | 44% | 65.8% |
| 400 ppm | 5% | 16 h | 43% | 65.5% |

The results show that the mixed bacteria fermentation broth can produce functional factors such as lactic acid, protease, cellulase, hemicellulase and the like, a synergistic effect of the functional factors may significantly shorten the steeping time and improve the starch yield.

Example 2

This example used for illustrating the combined effect of 2 *Bacillus* strains.

Obtaining a fermentation broth: 2 strains of *Bacillus coagulans* CGMCC No. 6382 and *Bacillus subtilis* CGMCC No. 13139 were respectively activated by an activated culture medium at a temperature of 50° C. and a rotational speed of 150 rpm for 24 hours, and then were inoculated into a seed culture medium according to the proportion of 6% (v/v) respectively, and subjected to a shake culture at a temperature of 50° C. for 16-20 hours, so as to obtain the mixed strain fermentation broth which was to be mixed with the steeping solution.

The corn was steeped according to the addition amount of SO$_2$ and mixed strain fermentation broth illustrated in Table 3, when to finish the steeping time was determined based on the criteria that the steeped corn can be cracked by hand and the germ can be extruded, the seed coat can be peeled off and was transparent and glossy, at this time, the water content of the wet corn was in accordance with the standard of 40-46%.

The steeping time, the water content of the steeped corn, and the starch yield were shown in Table 3.

TABLE 3

| SO$_2$ concentration | Mixed strain fermentation broth | Steeping time | Water content of the steeped corn | Starch yield |
|---|---|---|---|---|
| 3000 ppm | 0 | 48 h | 43% | 65.1% |
| 1200 ppm | 2% | 32 h | 44% | 66.0% |
| 800 ppm | 3% | 25 h | 43% | 65.6% |
| 400 ppm | 5% | 18 h | 45% | 65.3% |

The results show that the mixed bacteria fermentation broth can produce functional factors such as lactic acid, protease, cellulase, hemicellulase and the like, a synergistic effect of the functional factors may significantly shorten the steeping time and improve the starch yield, but the effects are slightly inferior to the synergistic effects of 4 strains.

Example 3

This example used for illustrating the effects of the *Bacillus licheniformis* CGMCC No. 13313 which was used alone.

Obtaining a fermentation broth: this strain was activated by an activated culture medium at a temperature of 50° C. and a rotational speed of 150 rpm for 24 hours, and then were inoculated into a seed culture medium according to proportion of 12% (v/v), and subjected to a shake culture at a temperature of 50° C. for 16-20 hours, to obtain the fermentation broth which was to be mixed with the steeping solution.

The corn was steeped according to the addition amount of SO$_2$ and mixed strain fermentation broth illustrated in Table 4, when to finish the steeping time was determined based on the criteria that the steeped corn can be cracked by hand and the germ can be extruded, the seed coat can be peeled off and was transparent and glossy, at this time, the water content of the wet corn was in accordance with the standard of 40-46%.

The steeping time, the water content of the steeped corn, and the starch yield were shown in Table 4.

TABLE 4

| SO$_2$ concentration | fermentation broth | Steeping time | Water content of the steeped corn | Starch yield |
|---|---|---|---|---|
| 3000 ppm | 0 | 48 h | 43% | 65.1% |
| 2000 ppm | 1% | 36 h | 44% | 65.4% |
| 1200 ppm | 2% | 34 h | 44% | 65.8% |
| 800 ppm | 3% | 28 h | 43% | 65.5% |
| 400 ppm | 5% | 26 h | 42% | 65.3% |

The results illustrate that when only the *Bacillus licheniformis* CGMCC No. 13313 is added, its effect of shortening the steeping time is obvious. The steeping effect is best when the concentration of SO$_2$ is 1200 ppm and the addition amount of the fermentation broth is 2%, and the steeping time allowing the steeped corn to reach the criteria is shortest when the concentration of SO$_2$ is 800 ppm and the addition amount of the fermentation broth is 3%.

Example 4

This example used for illustrating the effects of the *Bacillus licheniformis* CGMCC No. 15012 which was used alone.

Obtaining a fermentation broth: this strain was activated by an activated culture medium at a temperature of 50° C. and a rotational speed of 150 rpm for 24 hours, and then were inoculated into a seed culture medium according to the proportion of 12% (v/v), and subjected to a shake culture at a temperature of 50° C. for 16-20 hours, to obtain the fermentation broth which was to be mixed with the steeping solution.

The corn was steeped according to the addition amount of SO$_2$ and mixed strain fermentation broth illustrated in Table 5, when to finish the steeping time was determined based on the criteria that the steeped corn can be cracked by hand and the germ can be extruded, the seed coat can be peeled off and was transparent and glossy, at this time, the water content of the wet corn was in accordance with the standard of 40-46%.

The steeping time, the water content of the steeped corn, and the starch yield were shown in Table 5.

TABLE 5

| SO$_2$ concentration | fermentation broth | Steeping time | Water content of the steeped corn | Starch yield |
|---|---|---|---|---|
| 3000 ppm | 0 | 48 h | 43% | 65.1% |
| 2000 ppm | 1% | 36 h | 44% | 65.2% |
| 1200 ppm | 2% | 35 h | 45% | 65.7% |
| 800 ppm | 3% | 31 h | 45% | 65.2% |
| 400 ppm | 5% | 28 h | 46% | 65.0% |

The result illustrates that when only the *Bacillus licheniformis* CGMCC No. 15012 is added, its effect of shortening the steeping time is obvious, and when the fermentation broth is added in a much more amount, it also have the effect of improving the starch yield. The steeping effect is best when the concentration of $SO_2$ is 1200 ppm and the addition amount of the fermentation broth is 2%, and the steeping time allowing the steeped corn to reach the criteria is shortest when the concentration of $SO_2$ is 800 ppm and the addition amount of the fermentation broth is 3%.

Comparative Example 1

This comparative example used for illustrating the effects of the *Bacillus coagulans* CGMCC No. 6382 which was used alone.

Obtaining a fermentation broth: this strain was activated by an activated culture medium at a temperature of 50° C. and a rotational speed of 150 rpm for 24 hours, and then were inoculated into a seed culture medium according to the proportion of 12% (v/v), and subjected to a shake culture at a temperature of 50° C. for 16-20 hours, to obtain the fermentation broth which was to be mixed with the steeping solution.

The corn was steeped according to the addition amount of $SO_2$ and mixed strain fermentation broth illustrated in Table 6, when to finish the steeping time was determined based on the criteria that the steeped corn can be cracked by hand and the germ can be extruded, the seed coat can be peeled off and was transparent and glossy, at this time, the water content of the wet corn was in accordance with the standard of 40-46%.

The steeping time, the water content of the steeped corn, and the starch yield were shown in Table 6.

TABLE 6

| $SO_2$ concentration | fermentation broth | Steeping time | Water content of the steeped corn | Starch yield |
|---|---|---|---|---|
| 3000 ppm | 0 | 48 h | 43% | 65.1% |
| 2000 ppm | 1% | 42 h | 45% | 65.4% |
| 1200 ppm | 2% | 36 h | 46% | 65.5% |
| 800 ppm | 3% | 36 h | 42% | 64.8% |
| 400 ppm | 5% | 38 h | 40% | 64.1% |

The result illustrates that when only the *Bacillus coagulans* CGMCC No. 6382 is added, its effect of shortening the steeping time is good, but the steeping time cannot be shortened to be within 35 hours. The steeping effect is best when the concentration of $SO_2$ is 1200 ppm and the addition amount of the fermentation broth is 2%. When the addition amount of $SO_2$ is at a lower level of 800 ppm, corn can be steeped soft in a short time after the addition amount of fermentation broth is increased, but the starch yield is decreased, under such a condition, it has a poor effect of disrupt the network structure of the protein, is not conducive to the separation of the starch and the protein.

Comparative Example 2

This comparative example used for illustrating the effects of the *Bacillus subtilis* CGMCC No. 13139 which was used alone.

Obtaining a fermentation broth: this strain was activated by an activated culture medium at a temperature of 50° C. and a rotational speed of 150 rpm for 24 hours, and then were inoculated into a seed culture medium according to the proportion of 12% (v/v), and subjected to a shake culture at a temperature of 50° C. for 16-20 hours, to obtain the fermentation broth which was to be mixed with the steeping solution.

The corn was steeped according to the addition amount of $SO_2$ and mixed strain fermentation broth illustrated in Table 7, when to finish the steeping time was determined based on the criteria that the steeped corn can be cracked by hand and the germ can be extruded, the seed coat can be peeled off and was transparent and glossy, at this time, the water content of the wet corn was in accordance with the standard of 40-46%.

The steeping time, the water content of the steeped corn, and the starch yield were shown in Table 7.

TABLE 7

| $SO_2$ concentration | fermentation broth | Steeping time | Water content of the steeped corn | Starch yield |
|---|---|---|---|---|
| 3000 ppm | 0 | 48 h | 43% | 65.1% |
| 2000 ppm | 1% | 42 h | 44% | 65.3% |
| 1200 ppm | 2% | 42 h | 45% | 65.6% |
| 800 ppm | 3% | 42 h | 44% | 65.6% |
| 400 ppm | 5% | 42 h | 42% | 65.1% |

The result illustrates that when only the *Bacillus subtilis* CGMCC No. 13139 is added, it has a desirable effect of improving the starch yield under the circumstances that the concentration of $SO_2$ is 1200 ppm and the addition amount of the fermentation broth is 2%, and the concentration of $SO_2$ is 800 ppm and the addition amount of the fermentation broth is 3%, but the steeping time cannot be effectively reduced.

Comparative Example 3

The corn was steeped according to the method of Example 1, except that the 2% of the mixed fermentation broth added into the steeping solution was replaced with a mixed liquor containing lactic acid, protease, cellulase and hemicellulase, wherein the concentrations of lactic acid, protease, cellulase and hemicellulase in the mixed liquor were identical with the concentrations of lactic acid, protease, cellulase and hemicellulase in the system of Example 1 at the end of steeping process in which 2% of the mixed fermentation broth was added. The steeping time upon completing the steeping process was 35 hours, and the starch yield was 65.5%.

Using the complex bacteria of the present disclosure can reduce the content of $SO_2$ in the steeping solution from 2000-5000 ppm to 400-1200 ppm, shorten the steeping time from 48 hours to below 35 hours, and further improve the starch yield. When the complex bacteria consisting of 4 strains is used, the aforementioned effects can be further enhanced.

The above content describes in detail the preferred embodiments of the present disclosure, but the present disclosure is not limited thereto. A variety of simple modifications can be made in regard to the technical solutions of the present disclosure within the scope of the technical concept of the present disclosure, including a combination of individual technical features in any other suitable manner, such simple modifications and combinations thereof shall also be regarded as the content disclosed by the present disclosure, each of them falls into the protection scope of the present disclosure.

The invention claimed is:

1. A method for improving corn steeping effects, comprising: steeping corn in a steeping tank including a steeping solution containing a complex bacteria;
    wherein the complex bacteria comprises *Bacillus coagulans* CGMCC No. 6382, *Bacillus subtilis* CGMCC No. 13139, *Bacillus licheniformis* CGMCC No. 13313, and *Bacillus licheniformis* CGMCC No. 15012;

wherein said *Bacillus coagulans* CGMCC No. 6382 produces cellulase, hemicellulase, and lactic acid; said *Bacillus subtilis* CGMCC No. 13139 produces protease, cellulase, and lactic acid; said *Bacillus licheniformis* CGMCC No. 13313 produces protease, cellulase, hemicellulase, and lactic acid; and said *Bacillus licheniformis* CGMCC No. 15012 produces protease, cellulase, and hemicellulase;

wherein the steeping solution further comprises sulfur dioxide with a concentration of 400-1,200 ppm;

wherein time for the steeping is within a range of 16-30 hours; and wherein the steeping is performed at a temperature in a range of from 45-55° C.

2. The method of claim 1, wherein *Bacillus coagulans* CGMCC No. 6382 produces no amylase; *Bacillus subtilis* CGMCC No. 13139 produces no amylase; and *Bacillus licheniformis* CGMCC No. 15012 produces no amylase.

3. The method of claim 1, wherein bacterial cell ratio of *Bacillus coagulans* CGMCC No. 6382, *Bacillus subtilis* CGMCC No.13139, *Bacillus licheniformis* CGMCC No. 13313 and *Bacillus licheniformis* CGMCC No. 15012 is 1:0.1-10:0.1-10:0.1-10.

4. The method of claim 1, wherein the steeping solution has a content in a range of 200 mL to 500 mL based on 100 g of dry corn.

5. The method of claim 1, wherein an addition amount of the complex bacteria is 1-3 vol% calculated in a fermentation broth of the complex bacteria.

6. The method of claim 5, wherein the fermentation broth of the complex bacteria is prepared according to a method comprising: fermenting the complex bacteria in a culture medium containing peptone, yeast extract powder, sodium chloride, glucose and corn pulp filtrate, so as to obtain the fermentation broth.

7. The method of claim 6, wherein the culture medium comprises 0.8-1.2% of peptone, 0.4-0.6% of yeast extract powder, 0.4-0.6% of sodium chloride, 0.8-1.2% of glucose, 4-6% (v/v) of corn pulp filtrate based on the unit of g/100ml, and has a pH within a range of 5.5-6.5.

8. The method of claim 6, wherein the complex bacteria is cultured in the culture medium at a temperature of 45-55° C. and a rotation speed of 120-180 rpm for 20-30 hours, and then inoculated in a same fresh culture medium and cultured at a temperature of 45-55° C. and a rotation speed of 120-180 rpm for activation for 16-20 hours.

* * * * *